United States Patent
Hynes

(10) Patent No.: US 7,942,864 B2
(45) Date of Patent: May 17, 2011

(54) MEDICAL DEVICE INCLUDING A CATHETER PROVIDING WOUND EVACUATION AND MEDICINE DISPENSING FEATURES AND RELATED METHODS

(76) Inventor: Richard A. Hynes, Melbourne Beach, FL (US)

( * ) Notice: Subject to any disclaimer, the term of this patent is extended or adjusted under 35 U.S.C. 154(b) by 1475 days.

(21) Appl. No.: 11/150,512

(22) Filed: Jun. 10, 2005

(65) Prior Publication Data

US 2007/0005004 A1    Jan. 4, 2007

(51) Int. Cl.
*A61M 25/00*      (2006.01)
(52) U.S. Cl. .............. 604/523; 604/93.01; 604/191
(58) Field of Classification Search ........... 604/96.01, 604/164.01, 523, 43, 282, 275–279, 93.01, 604/191
See application file for complete search history.

(56) References Cited

U.S. PATENT DOCUMENTS

| | | | |
|---|---|---|---|
| 3,771,527 A | 11/1973 | Ruisi | 128/350 R |
| 3,823,720 A | 7/1974 | Tribble | 128/350 R |
| 4,364,394 A | 12/1982 | Wilkinson | 604/96 |
| 4,781,678 A | 11/1988 | de Couët et al. | 604/45 |
| 5,221,255 A * | 6/1993 | Mahurkar et al. | 604/43 |
| 5,318,517 A | 6/1994 | Reiman | 604/43 |
| 5,320,599 A | 6/1994 | Griep et al. | 604/35 |
| 5,558,634 A | 9/1996 | Mitchell | 604/35 |
| 5,616,121 A | 4/1997 | McKay | 604/35 |
| 5,785,678 A | 7/1998 | Griep et al. | 604/28 |
| 6,325,788 B1 | 12/2001 | McKay | 604/506 |
| 6,569,839 B1 | 12/2003 | McKay | 514/54 |
| 2003/0069551 A1 | 4/2003 | Bradley, III et al. | 604/276 |
| 2004/0030281 A1 | 2/2004 | Goble et al. | 604/28 |
| 2004/0054338 A1 | 3/2004 | Bybordi et al. | 604/313 |

* cited by examiner

*Primary Examiner* — Kevin C Sirmons
*Assistant Examiner* — Phillip Gray
(74) *Attorney, Agent, or Firm* — Allen, Dyer, Doppelt, Milbrath & Gilchrist, P.A.

(57) ABSTRACT

A medical device including a catheter having a proximal end portion, a distal end portion, and a medial portion extending therebetween. The proximal end portion may have at least one evacuation lumen extending longitudinally therethrough, and at least one evacuation opening extending laterally therethrough and intersecting the evacuation lumen to permit evacuation of waste from a wound. The distal end portion may have at least one medicine dispensing lumen extending longitudinally therethrough and at least one medicine dispensing opening extending laterally therethrough and intersecting the medicine dispensing lumen to permit dispensing of medicine into the wound. The medial portion may have at least one medicine reservoir lumen therein connected in fluid communication with the medicine dispensing lumen of the distal end portion. Also, a barrier may longitudinally separate the evacuation lumen and the medicine reservoir lumen.

22 Claims, 4 Drawing Sheets

MEDICAL DEVICE INCLUDING A CATHETER PROVIDING WOUND EVACUATION AND MEDICINE DISPENSING FEATURES AND RELATED METHODS

FIELD OF THE INVENTION

The present invention relates to the field of medical devices, and, more particularly, to catheters and related methods.

BACKGROUND OF THE INVENTION

Catheters are widely used for evacuating waste from post-operative wounds, particularly deep wounds. Such deep wounds may be created during spinal or other types of surgery, for example. These wounds need to be drained because waste (e.g., blood) accumulation inside the wound may result in pain and/or infection.

Various types of drains have been developed for evacuating fluids from wounds. For example, U.S. Pat. No. 3,771,527 to Ruisi discloses a surgical drainage tube which has inner and outer concentric tube portions, each having fluid apertures. A cap seals the proximal end of the outer tube portion, and the inner tube portion extends through the cap. A proximal end of the inner tube is connected to a suction source for removing fluid from the wound. Fluid from the wound enters first through the apertures in the outer tube, and then through the apertures in the inner tube where it is removed by the suction. The cap is made of a penetrable, self-sealing material, such as pregnable latex, which allows a hypodermic needle to be inserted therethrough to introduce a fluid into the outer tube, such as an antibiotic solution or a sterile flushing solution. One potential drawback of this arrangement, however, is that medicine injected into the catheter may be evacuated through the apertures in the inner tube. This may result in wasted medicine, and it may make it difficult to provide a steady supply of medicine into the wound, for example.

U.S. Patent Application Publication No. 2004/0030281 is directed to an infusion and aspiration catheter assembly for a surgical wound site. The catheter assembly includes an infusion catheter and an aspiration catheter, each having ports located at the distal end of thereof. The infusion catheter extends through the aspiration catheter and beyond the distal end thereof. This is done so that the distal end of the infusion catheter can be placed in a different location than the distal end of the aspiration catheter, such as on opposing sides of a patient's knee. The infusion catheter is connected at the proximal end to a pump, which is connected to a medication reservoir. The medicinal fluid delivered via the infusion catheter may be an analgesic, anesthetic, antibiotic, antiseptic, anticoagulant, anti-inflammatory, or combinations thereof. Moreover, the aspiration catheter is connected to an aspiration reservoir, and suction created by a suction pump connected thereto causes excess fluid to be removed from the wound site. Similar infusion/drain catheter systems for delivery of pain medication to a specific location are disclosed in U.S. Pat. Nos. 6,325,788; 5,616,121; and 6,569,839, for example.

Another example is disclosed in U.S. Pat. No. 3,823,720 to Tribble. This patent discloses a surgical drain which includes a drainage catheter and an irrigation catheter wrapped within a nylon net. The irrigation catheter may be used either for introducing an irrigating fluid, or for an antibiotic or other medicinal liquid. U.S. Pat. No. 5,558,634 to Mitchell discloses an apparatus for the removal of viscoelastic material from an eye chamber which includes an irrigation lumen and an aspiration lumen. In one embodiment, the irrigation lumen is within the aspiration lumen and extends outwardly therefrom.

A closed wound drainage system is disclosed in U.S. Patent Application Publication No. 2004/0054338. A flexible, porous pouch is inserted into a wound. Exudates are removed via the pores in the pouch through an aspiration tube, which is connected to a portable drain/suction unit. Another tube may also be used for pumping medications, such as antibiotics, into the pouch. Moreover, the pouch may also include beads and fillers therein which are antibacterial in nature. The pouch and tube(s) are sealed in the wound by a flexible sealing gel, such as a hydro-colloid, silicon, or a lyogel.

One drawback of such prior art catheter systems which are connected to an external medicine source (e.g., a pump) for receiving medicine is that this requires multiple tubes to be connected to the catheter, which increases the chances of tangling the tubes. Moreover, a separate pump may require relatively frequent monitoring, and it may also limit the patient's mobility and/or movement. Further, medication tubes which run to an external medicine pump may unknowingly be bent or crimped, which undesirably restricts the flow of medicine to the wound.

SUMMARY OF THE INVENTION

In view of the foregoing background, it is therefore an object of the present invention to provide a catheter for providing enhanced wound evacuation and medicine dispensing features and related methods.

This and other objects, features, and advantages in accordance with the present invention are provided by a medical device comprising a catheter having a proximal end portion, a distal end portion, and a medial portion extending therebetween. In particular, the proximal end portion may have at least one evacuation lumen extending longitudinally therethrough, and at least one evacuation opening extending laterally therethrough and intersecting the at least one evacuation lumen to permit evacuation of waste from a wound. Moreover, the distal end portion may have at least one medicine dispensing lumen extending longitudinally therethrough and at least one medicine dispensing opening extending laterally therethrough and intersecting the at least one medicine dispensing lumen to permit dispensing of medicine into the wound. The medial portion may have at least one medicine reservoir lumen therein connected in fluid communication with the at least one medicine dispensing lumen of the distal end portion. Also, a barrier may longitudinally separate the at least one evacuation lumen and the at least one medicine reservoir lumen.

Accordingly, the medical reservoir lumen may be filled with a volume of medicine, such as an analgesic and/or antibiotic, for example. As a result, an external medicine pump and associated tubing need not be connected to the catheter to provide a continuous dilution of medicine into the wound. Thus, a patient may experience a relatively high degree of mobility while the catheter is in place. Moreover, there is no tube connecting the catheter to an external medicine pump to become crimped and thus restrict the flow of medicine. In addition, a piston may be carried within the medial portion for pushing the volume of medicine into the at least one medicine reservoir lumen. Also, a spring may be carried within the medical portion between the piston and the proximal end portion.

The catheter may further include an evacuation tube port connected to the proximal end portion of the catheter and in fluid communication with the at least one evacuation lumen.

Thus, a tube may advantageously be connected between the evacuation tube port and a waste collection device or reservoir.

The at least one evacuation opening may be larger than the at least one medicine dispensing opening, for example. Accordingly, the waste is evacuated relatively quickly from the wound, and the medicine flows slowly into the wound at a desired rate. Moreover, the at least one evacuation opening may comprise a plurality thereof, and the at least one medicine dispensing opening may similarly comprise a plurality thereof. By way of example, the catheter may comprise plastic.

A wound treatment method aspect of the invention may include providing a catheter, such as the one described briefly above. The method may further include inserting the catheter in a wound proximal end portion first.

DETAILED DESCRIPTION OF THE PREFERRED EMBODIMENTS

Figure 1:
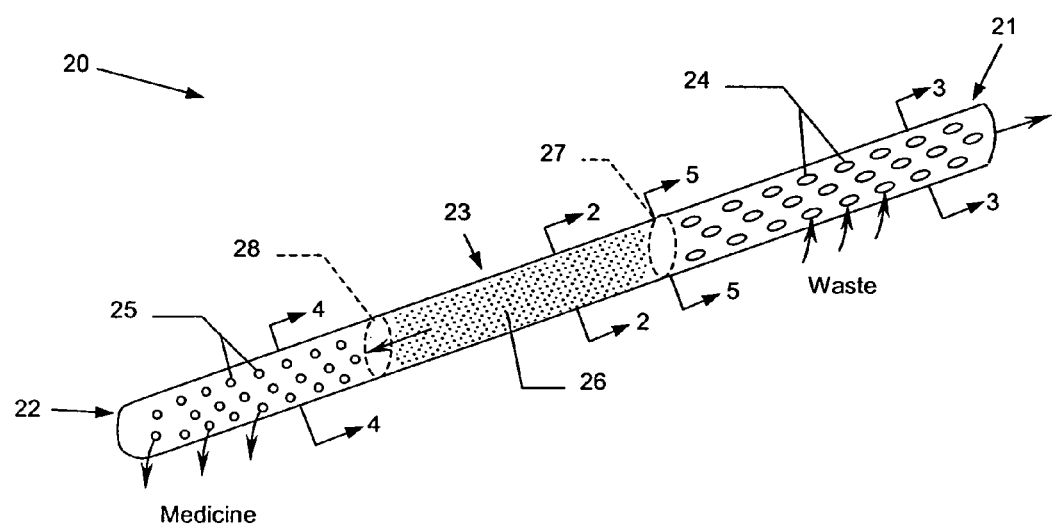
FIG. 1 is a schematic perspective view of a catheter in accordance with the present invention.
Figure 2:
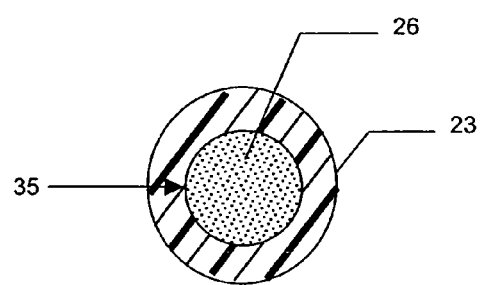
FIGS. 2-5 are cross-sectional views of the catheter of FIG. 1 taken along lines 2-2 through 5-5, respectively.
Figure 3:
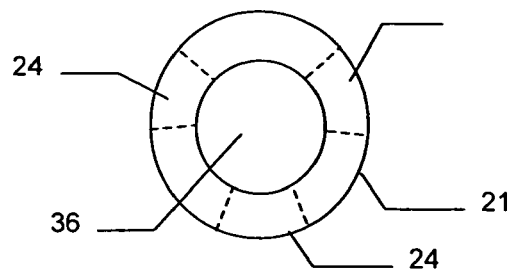
Figure 4:
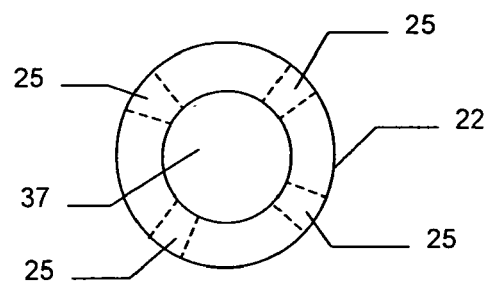
Figure 5:
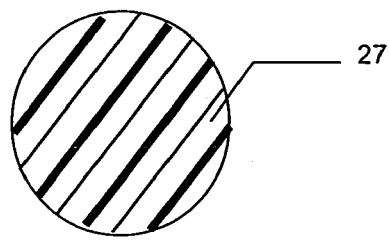

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, and prime notation is used to indicate similar elements in alternate embodiments.

Referring initially to FIGS. 1-5, a medical device for treating wounds, and more particularly, surgical wounds, is provided by a catheter 20. The catheter 20 is particularly advantageous for use in deep spinal wounds resulting from spinal surgeries, for example. However, the catheter 20 may also be used with other types of wounds as well, as will be appreciated by those skilled in the art. In particular, the catheter 20 may be used as a post-operative catheter to provide evacuation of unwanted waste from the wound, while at the same time providing a slow, continuous flow of medicine to the wound over a given period of time. For example, the catheter 20 may typically supply a slow flow of medicine to the wound until about the third to fifth post-operative day when the catheter is to be removed, although other durations may be used in different applications.

The catheter 20 is generally cylindrical in shape and has a proximal end portion 21, a distal end portion 22, and a medial portion 23 extending therebetween. It should be noted that the catheter 20 may take other shapes in different embodiments, however. The proximal end portion 21 has one or more evacuation lumens 36 (FIG. 3) extending longitudinally therethrough. Moreover, one or more evacuation openings 24 extend laterally through the proximal end portion 21 and intersect the evacuation lumen(s) 36 to permit evacuation of waste (e.g., blood) from a wound. In the illustrated embodiment, a plurality of evacuation openings 24 intersect a single evacuation lumen 36.

The distal end portion 22 illustratively has one or more medicine dispensing lumens 37 (FIG. 4) extending longitudinally therethrough, and one or more medicine dispensing openings 25 extending laterally therethrough and intersecting the medicine dispensing lumen(s) 37 to permit dispensing of the medicine into the wound. Once again, in the illustrated embodiment a plurality of medicine dispensing openings 25 intersect a single medicine dispensing lumen 37.

Furthermore, the medial portion 23 illustratively has one or more medicine reservoir lumens 35 (FIG. 2) therein connected in fluid communication with the medicine dispensing lumen 37 of the distal end portion 22, which in the illustrated embodiment is a single medicine reservoir lumen 35. A barrier 27 longitudinally separates the evacuation lumen 36 and the medicine reservoir lumen 35. This is so that medicine within the medicine reservoir lumen 35 is not evacuated out of the catheter 20 through the evacuation lumen 36. The evacuation of waste from the wound will be discussed further below.

The medical reservoir lumen 35 is filled with a volume of medicine, such as an analgesic and/or antibiotic, for example. Various types of antibiotics, analgesics, and other medicines may be used in the catheter 20 which are well known to those skilled in the art. By way of example, the barrier 27 may be made out of a self-sealing material so that a surgeon or medical attendant can puncture and fill the medicine reservoir lumen 35 with the desired medicine(s) using a needle and syringe before the catheter 20 is inserted into the wound.

The catheter 20 may further include a second barrier 28 which, with the first barrier 27, encloses the volume of medicine within the medicine reservoir lumen 35. In some embodiments, the medicine reservoir lumen 35 may be pre-filled with a particular medicine(s), e.g., it may be filled during the manufacturing process. As such, the surgeon would order the appropriate catheter 20 with the desired medicine for a given post-operative treatment. In this case, the second membrane 28 may be made of a material which, when punctured before insertion into the patient's wound, allows the medicine to be dispensed via the medicine dispensing lumen 37 and the medicine dispensing openings 25.

In an alternate embodiment, the first and second barriers 27, 28 may be opposing ends of a bladder inserted into the medical reservoir lumen 35, for example. In still another embodiment, the various portions 21, 22, and/or 23 of the catheter 20 may be provided in separate interchangeable sections which are connected together (e.g., snapped, screwed, etc.) for a particular application. This allows the interchanging of different medial portions having different medicine types. Moreover, various lengths of the portions 21, 22, and/or 23 may be used depending upon the wound depth, the amount of medicine required, etc. In addition, different distal end portions 22 and/or proximal end portions 21 may be used depending upon the size of the openings 25 or 24 required, for example.

As will be appreciated by those of skill in the art, since medicine is retained within the medicine reservoir lumen 35, an external medicine source (e.g., a pump) and associated tubing need not be connected to the catheter 20 to provide a continuous flow of medicine into the wound. That is, the relative dimensions of the medical reservoir lumen 35, the medicine dispending openings 25, and/or the viscosity of the medicine being dispensed may be tailored to provide a desired flow rate and for a desired period without the need for an external medicine source. Thus, since no external medicine source or tubing therefor is required, a patient may experience a relatively high degree of mobility even while the catheter 20 is in place. Moreover, since a separate medicine flow tube need not be used, tube crimping and the resulting restriction of medicine flow may be avoided.

Figure 6:
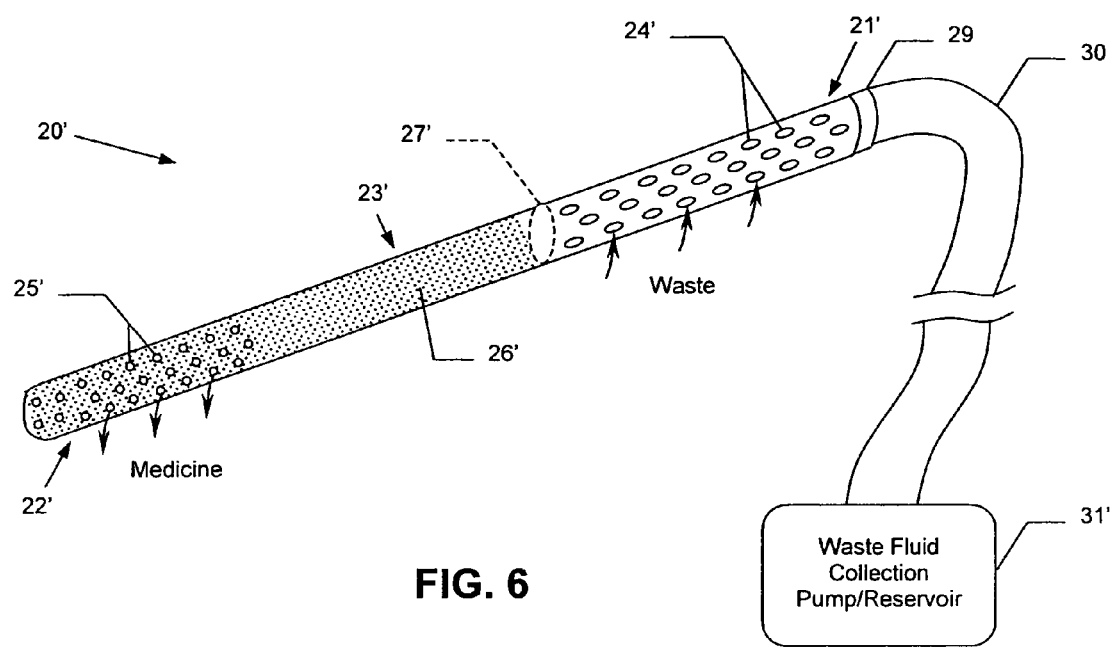
FIG. 6 is a schematic perspective view of an alternate embodiment of the catheter of FIG. 1 in accordance with the present invention.

Turning now additionally to FIG. 6, in another embodiment the second barrier 28 between the medicine reservoir lumen 35 and the medicine dispensing lumen 37 may be omitted, and an evacuation tube port 29' may be connected to the proximal end portion 21' of the catheter 20'. The evacuation tube port 29' is in fluid communication with the evacuation openings 24'. A first end of an evacuation tube 30' is connected to the evacuation tube port 29', and the second end of the evacuation tube is connected to a waste fluid collection reservoir 31'. By way of example, the waste fluid collection reservoir 31' may be a medical waste collection bag, although other suitable collection devices or suction pumps may also be used.

In this way, the catheter 20' not only provides medicines to the wound to promote healing and/or pain relief, but potentially harmful blood or other waste fluids which would otherwise accumulate in the wound may be evacuated to further decrease the likelihood of infection, for example. Preferably, the evacuation openings 24 are larger than the medicine dispensing openings 25. This is so that waste is evacuated relatively quickly from the wound, but the medicine eludes slowly into the wound at a desired rate.

Figure 7:
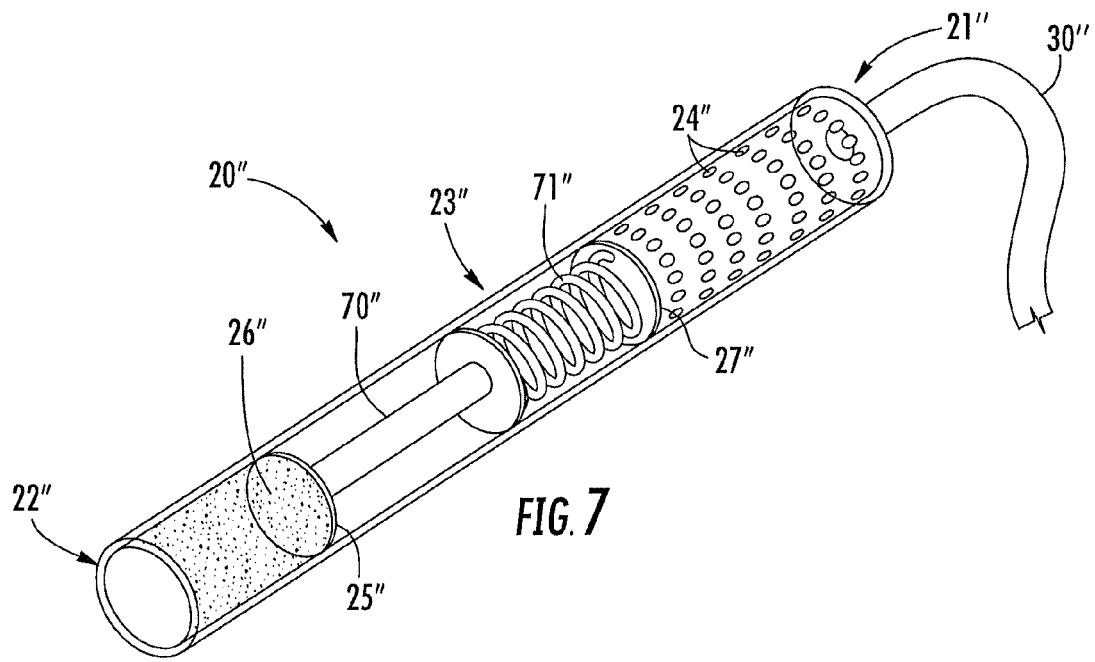
FIG. 7 is a schematic perspective view of yet another alternate embodiment of the catheter of FIG. 1 in accordance with the present invention.

Referring now to FIG. 7, still another embodiment of the catheter 20" includes a piston 70" and a spring 71" carried within the medial portion 23". More particularly, the spring 71" is positioned between the barrier 27" and the piston 70" for biasing the piston to push the medicine 26" into the distal end portion 22". In the illustrated embodiment, the medicine 26" is a solid pellet that is pushed by the piston 70" so that it is adjacent the medicine dispensing openings 26" to dissolve and slowly elude into the wound.

Figure 8:
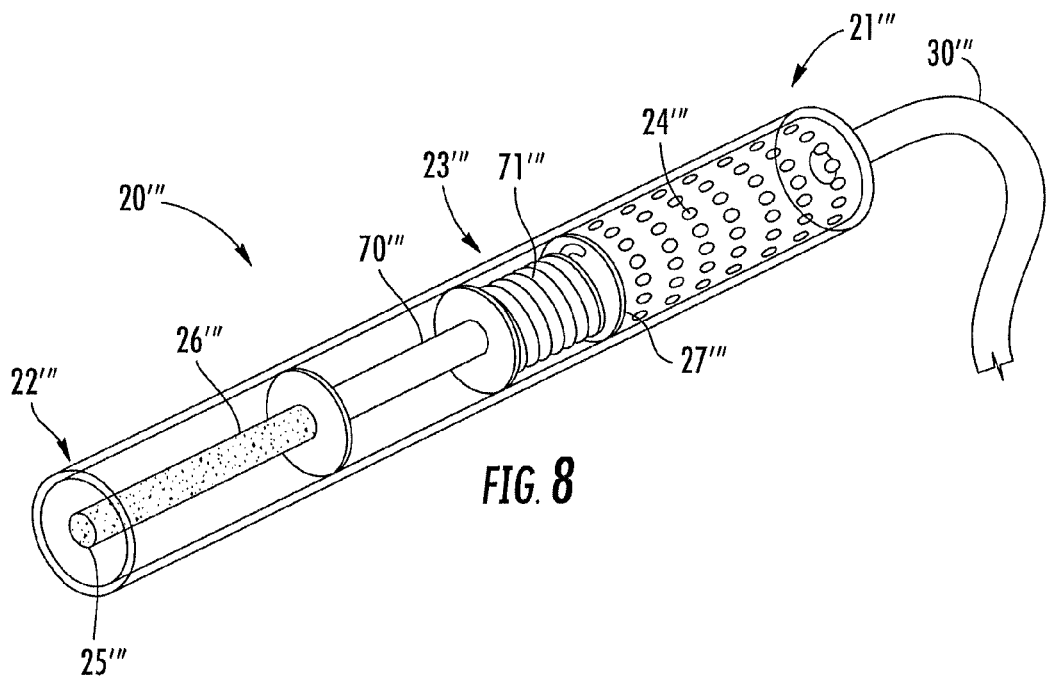
FIG. 8 is a schematic perspective view of still another alternate embodiment of the catheter of FIG. 1 in accordance with the present invention.

In yet another embodiment illustrated in FIG. 8, the distal end portion 22''' has a single medicine dispensing opening 26''', and the piston 70''' forces the medicine pellet 26''' through the medicine dispensing opening into the wound. That is, as the tip of the medicine pellet 26''' dissolves the piston 70''' forces more of the pellet into the wound. Of course, it will be appreciated that configurations other than those shown herein by way of example may also be used.

In a typical spinal wound application the catheter 20 may be about 2-8 cm in length and have a diameter of about 5-20 mm, for example. Further, the evacuation openings 24 and/or the dispensing openings 25 may have a diameter of less than about 5 mm. The catheter may be made of any suitable material for the particular wound application for which it is to be used. One exemplary material is plastic. Of course, it will be appreciated by those skilled in the art that different materials and dimensions may be used for the catheter 20 in different applications.

A wound treatment method aspect of the invention may include providing a catheter 20, such as the one described briefly above, and inserting the catheter in a wound proximal end portion 22 first. Moreover, the medicine reservoir lumen 35 may be filled with medicine prior to inserting the catheter 20, and an evacuation tube 30' may be connected to an evacuation tube port 29' for evacuating waste from the wound to a waste fluid collection reservoir 31', as discussed further above.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A medical device comprising:
   a catheter having a proximal end portion, a distal end portion, and a medial portion extending therebetween;
   said proximal end portion having at least one evacuation lumen extending longitudinally therethrough and at least one evacuation opening extending laterally therethrough and intersecting the at least one evacuation lumen to permit evacuation of waste from a wound;
   said distal end portion having at least one medicine dispensing lumen extending longitudinally therethrough and at least one medicine dispensing opening extending laterally therethrough and intersecting the at least one medicine dispensing lumen to permit dispensing of medicine into the wound;
   said medial portion having at least one medicine reservoir lumen therein connected in fluid communication with the at least one medicine dispensing lumen of said distal end portion;
   the at least one evacuation lumen, the at least one medicine dispensing lumen and the at least one medicine reservoir lumen sharing a common central longitudinal axis; and
   a barrier transverse to the common central longitudinal axis and longitudinally separating said at least one evacuation lumen and said at least one medicine reservoir lumen.

2. The medical device of claim 1 further comprising a volume of medicine within the at least one medicine reservoir lumen.

3. The medical device of claim 2 wherein the medicine comprises at least one antibiotic.

4. The medical device of claim 2 wherein the medicine comprises at least one analgesic.

5. The medical device of claim 2 further comprising a piston carried within said medial portion for pushing the volume of medicine into the at least one medicine reservoir lumen.

6. The medical device of claim 5 further comprising a spring carried within said medial portion between said piston and the proximal end portion.

7. The medical device of claim 1 further comprising an evacuation tube port connected to said proximal end portion of said catheter and in fluid communication with the at least one evacuation lumen.

8. The medical device of claim 1 wherein the at least one evacuation opening is larger than the at least one medicine dispensing opening.

9. The medical device of claim 1 wherein the at least one evacuation opening comprises a plurality thereof, and wherein the at least one medicine dispensing opening comprises a plurality thereof.

10. The medical device of claim 1 wherein said catheter comprises plastic.

11. A medical device comprising:
   a catheter having a proximal end portion, a distal end portion, and a medial portion extending therebetween;
   said proximal end portion having at least one evacuation lumen extending longitudinally therethrough and a plurality of evacuation openings extending laterally therethrough and intersecting the at least one evacuation lumen to permit evacuation of waste from a wound;

said distal end portion having at least one medicine dispensing lumen extending longitudinally therethrough and a plurality of medicine dispensing openings extending laterally therethrough and intersecting the at least one medicine dispensing lumen to permit dispensing of medicine into the wound;

said medial portion having at least one medicine reservoir lumen therein connected in fluid communication with the at least one medicine dispensing lumen of said distal end portion;

the at least one evacuation lumen, the at least one medicine dispensing lumen and the at least one medicine reservoir lumen sharing a common central longitudinal axis;

a volume of medicine within the at least one medicine reservoir lumen; and a barrier transverse to the common central longitudinal axis and longitudinally separating said at least one evacuation lumen and said at least one medicine reservoir lumen.

12. The medical device of claim 11 wherein the medicine comprises at least one antibiotic.

13. The medical device of claim 11 wherein the medicine comprises at least one analgesic.

14. The medical device of claim 11 further comprising an evacuation tube port connected to said proximal end portion of said catheter and in fluid communication with the at least one evacuation lumen.

15. The medical device of claim 11 wherein the evacuation openings are larger than the medicine dispensing openings.

16. A wound treatment method comprising:
providing a catheter having a proximal end portion, a distal end portion, and a medial portion extending therebetween,
the proximal end portion having at least one evacuation lumen extending longitudinally therethrough and at least one evacuation opening extending laterally therethrough and intersecting the at least one evacuation lumen to permit evacuation of waste from a wound,
the distal end portion having at least one medicine dispensing lumen extending longitudinally therethrough and at least one medicine dispensing opening extending laterally therethrough and intersecting the at least one medicine dispensing lumen to permit dispensing of medicine into the wound,
the medial portion having at least one medicine reservoir lumen therein connected in fluid communication with the at least one medicine dispensing lumen of the distal end portion,
the at least one evacuation lumen, the at least one medicine dispensing lumen and the at least one medicine reservoir lumen sharing a common central longitudinal axis; and
the at least one evacuation lumen and the at least one medicine reservoir lumen being longitudinally separated by a barrier positioned transverse to the common central longitudinal axis, and
inserting the catheter in the wound, proximal end portion first.

17. The method of claim 16 further comprising filling the at least one medicine reservoir lumen with a volume of medicine.

18. The method of claim 17 wherein the medicine comprises at least one antibiotic.

19. The method of claim 17 wherein the medicine comprises at least one analgesic.

20. The method of claim 16 wherein the catheter further comprises an evacuation tube port connected to the proximal end portion of the catheter and in fluid communication with the at least one evacuation lumen; and further comprising connecting an evacuation tube to the evacuation tube port.

21. The method of claim 16 wherein the at least one evacuation opening is larger than the at least one medicine dispensing opening.

22. The method of claim 16 wherein the at least one evacuation opening comprises a plurality thereof, and wherein the at least one medicine dispensing opening comprises a plurality thereof.

* * * * *